United States Patent
Baumgart et al.

(10) Patent No.: US 12,178,629 B2
(45) Date of Patent: Dec. 31, 2024

(54) METHOD AND SYSTEM FOR AUTOMATIC DEPLOYMENT OF IMAGE RESTORATION PARAMETERS

(71) Applicant: CANON MEDICAL SYSTEMS CORPORATION, Tochigi (JP)

(72) Inventors: John Baumgart, Vernon Hills, IL (US); Yi Hu, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 362 days.

(21) Appl. No.: 17/341,622

(22) Filed: Jun. 8, 2021

(65) Prior Publication Data

US 2022/0386977 A1    Dec. 8, 2022

(51) Int. Cl.
*G06K 9/00*     (2022.01)
*A61B 6/00*     (2006.01)
*G06T 7/00*     (2017.01)

(52) U.S. Cl.
CPC .............. *A61B 6/52* (2013.01); *G06T 7/0002* (2013.01); *G06T 2207/10116* (2013.01); *G06T 2207/20084* (2013.01); *G06T 2207/30004* (2013.01); *G06T 2207/30168* (2013.01)

(58) Field of Classification Search
CPC .................... A61B 6/52; G06T 7/0002; G06T 2207/10116; G06T 2207/20084; G06T 2207/30004; G06T 2207/30168
USPC .......................................................... 382/128
See application file for complete search history.

(56) References Cited

U.S. PATENT DOCUMENTS

| 2019/0005686 | A1 | 1/2019 | Liu |
| 2019/0220975 | A1* | 7/2019 | Hsieh .................. G06N 3/08 |
| 2019/0251713 | A1* | 8/2019 | Chen .................. A61B 6/482 |
| 2020/0065940 | A1 | 2/2020 | Tang et al. |
| 2020/0104720 | A1 | 4/2020 | Bao et al. |

OTHER PUBLICATIONS

Wu, et al. ; Combined spatial and temporal deep learning for image noise reduction of fluoroscopic x-ray sequences Proceedings of SPIE ; SPIE Medical Imaging, 202, Houston TX ; Physics of Medical Imaging ; 8 Pages.

Wu, et al. ; Fluoroscopic Image Denoising with Feature Preserving Residual Noise Learning ; Association of Computing Machinery ; 2019 ; 5 Pages.

* cited by examiner

*Primary Examiner* — Jonathan S Lee
(74) *Attorney, Agent, or Firm* — Oblon, McClelland, Maier & Neustadt, L.L.P.

(57) ABSTRACT

A method includes obtaining, at a local imaging system, projection data for an object representing an intensity of radiation detected along a plurality of rays through the object using a first set of imaging parameters; transmitting an image quality dataset related to the obtained projection data to a remote server; generating, via the remote server, localized restoration information based on the received image quality dataset; transferring the localized restoration information from the remote server to the local imaging system; and updating the local imaging system using the localized restoration information.

25 Claims, 7 Drawing Sheets

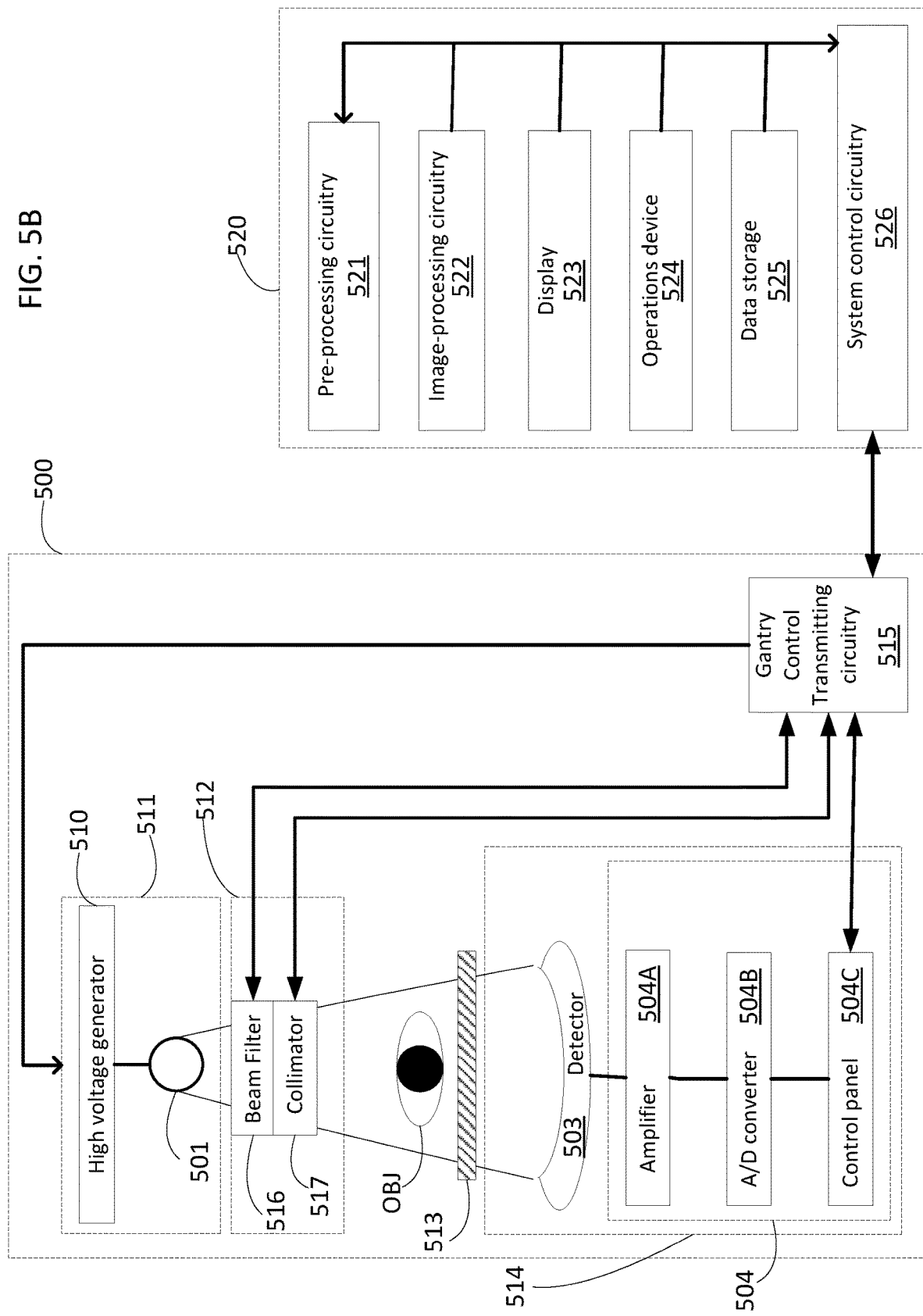

METHOD AND SYSTEM FOR AUTOMATIC DEPLOYMENT OF IMAGE RESTORATION PARAMETERS

FIELD OF THE INVENTION

This disclosure relates to a method and imaging system for noise characteristic determination of local imaging systems, image restoration model determination, and automatic deployment of image restoration parameters to the local imaging systems.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Optimal image quality of X-ray images can be dependent on a system being properly calibrated for its unique components and environment. When myriad installations of X-ray systems are all maintained separately, used differently, and are at different time points in their lifespans, the calibration of said systems can vary, leading to different imaging parameters. Current practice includes local calibration procedures that determine relevant parameters and factors, such as defective pixels, appropriate signal gain and offsets to be applied, etc., but do not attempt to model the system's noise attributes or point spread function to be leveraged by noise reduction or image restoration processes. One source of variation can be attributed to assigning different service technicians for said local calibration procedure. Furthermore, since X-ray tubes age differently, the expectation is that there may be different noise characteristics that develop over time in different systems. Thus, a method and system without the involvement of the service technician in maintaining and calibrating the system is desired. In particular, a method and system for AI-based image restoration of site-specific data and automatic updating of the site-specific systems is desired.

SUMMARY

The present disclosure relates to a method, including: obtaining, at a local imaging system, projection data for an object representing an intensity of radiation detected along a plurality of rays through the object using a first set of imaging parameters; transmitting an image quality dataset related to the obtained projection data to a remote server; generating, via the remote server, localized restoration information based on the received image quality dataset; transferring the localized restoration information from the remote server to the local imaging system; and updating the local imaging system using the localized restoration information.

The present disclosure additionally relates to an imaging system, including: processing circuitry configured to obtain, at the local imaging system, projection data for an object representing an intensity of radiation detected along a plurality of rays through the object using a first set of imaging parameters; transmit an image quality dataset related to the obtained projection data to a remote server; generate, via the remote server, localized restoration information based on the received image quality dataset; transfer the localized restoration information from the remote server to the local imaging system; and update the local imaging system using the localized restoration information.

Note that this summary section does not specify every embodiment and/or incrementally novel aspect of the present disclosure or claimed invention. Instead, this summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein:

FIG. 5B is a block diagram of an exemplary X-ray apparatus that can be used to perform the methods described herein, according to an embodiment of the present disclosure.

DETAILED DESCRIPTION

Figure 1:
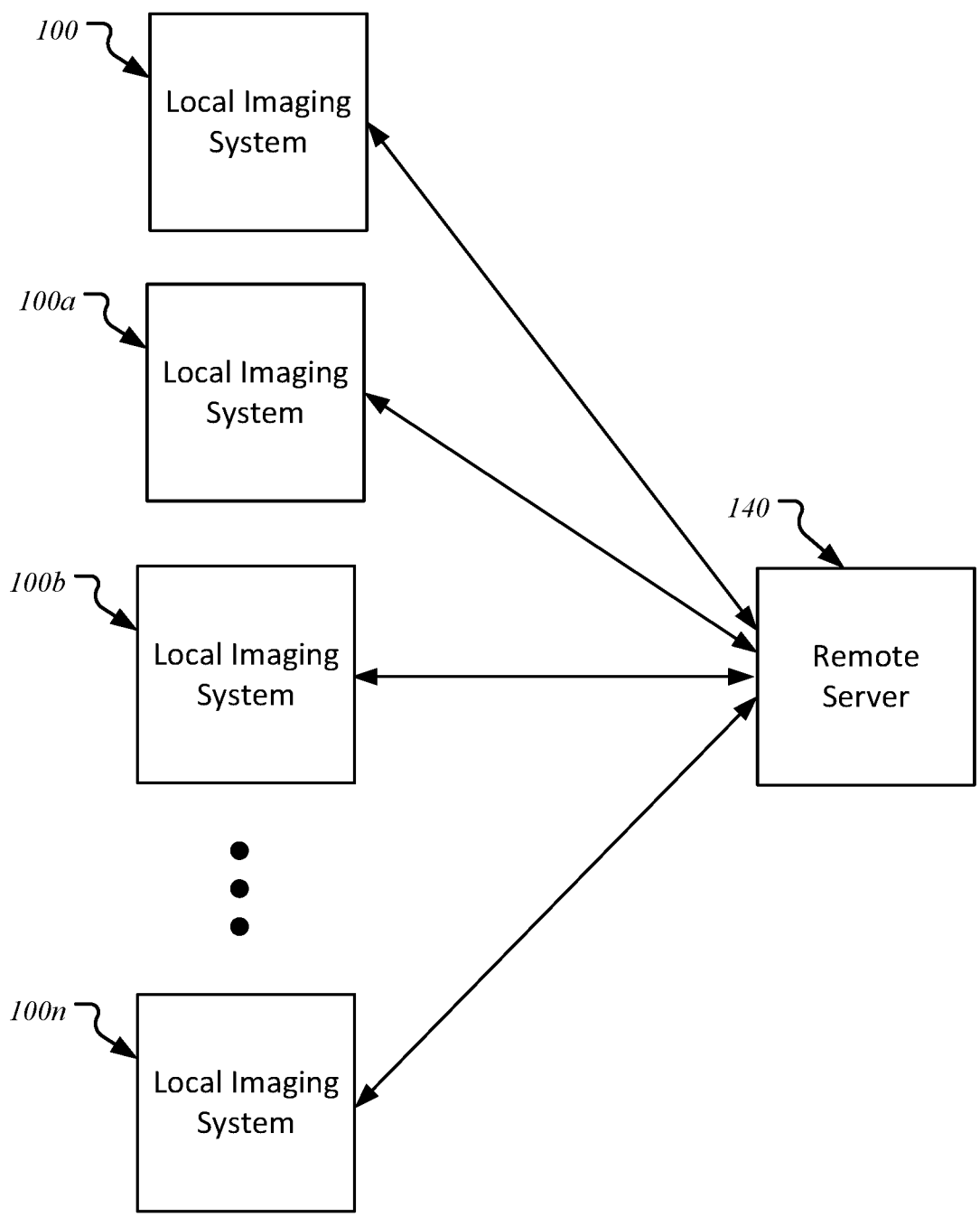
FIG. 1 shows a schematic of a system for automatic deployment of image restoration parameters including multiple local systems, according to an embodiment of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. Further, spatially relative terms, such as "top," "bottom," "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The order of discussion of the different steps as described herein has been presented for clarity sake. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

Described herein is a method and system for automatic deployment of image restoration parameters using an AI-based image restoration process using the data collected from site-specific systems. The AI-based image restoration process can include a neural network using the collected data as the training dataset to update an image restoration model. The custom training neural network can be more sensitive or adapt matters to very a specific type of image quality degradation, such as noise, that can be attributed to a particular system, with the expectation that different systems will behave differently. When the neural network is trained and validated, it then pushes an update on to the system and gradually improves the image restoration or recalibrates the image restoration for the system. Advantageously, the system and method described herein enable tailoring of image correction/restoration processes to individual systems (or even system components) and the ability to do this automatically, not requiring further intervention by a local service engineer once a system is properly calibrated. As previously described, this is especially advantageous for systems implemented at varying time-points having different lifespans of operation with components at vary ages, wherein all systems can be calibrated according to a single standard.

FIG. 1 shows a schematic of a system for automatic deployment of image restoration parameters including multiple local systems, according to an embodiment of the present disclosure. In an embodiment, the system can include a local imaging system 100 and a remote server 140. The remote server 140 can be communicatively coupled to the local imaging system 100. For example, the remote server 140 can be connected to the local imaging system 100 via Ethernet, satellite link, Wi-Fi (2.4 GHz, 5 GHz, 6 GHz), cellular (3G, 4G, 5G), or any combination thereof, among others. Notably, more than one of the local imaging system 100 can be connected to the remote server 140 (as shown). For example, a second local imaging system 100a to an $n^{th}$ local imaging system 100n can be connected to the remote server 140. As mentioned previously, the local imaging system 100 can range in lifespan out in the field. That is, the local imaging system 100, the second local imaging system 100a, the $n^{th}$ local imaging system 100n, and those in between need not be all the same age or the same model.

Figure 2:
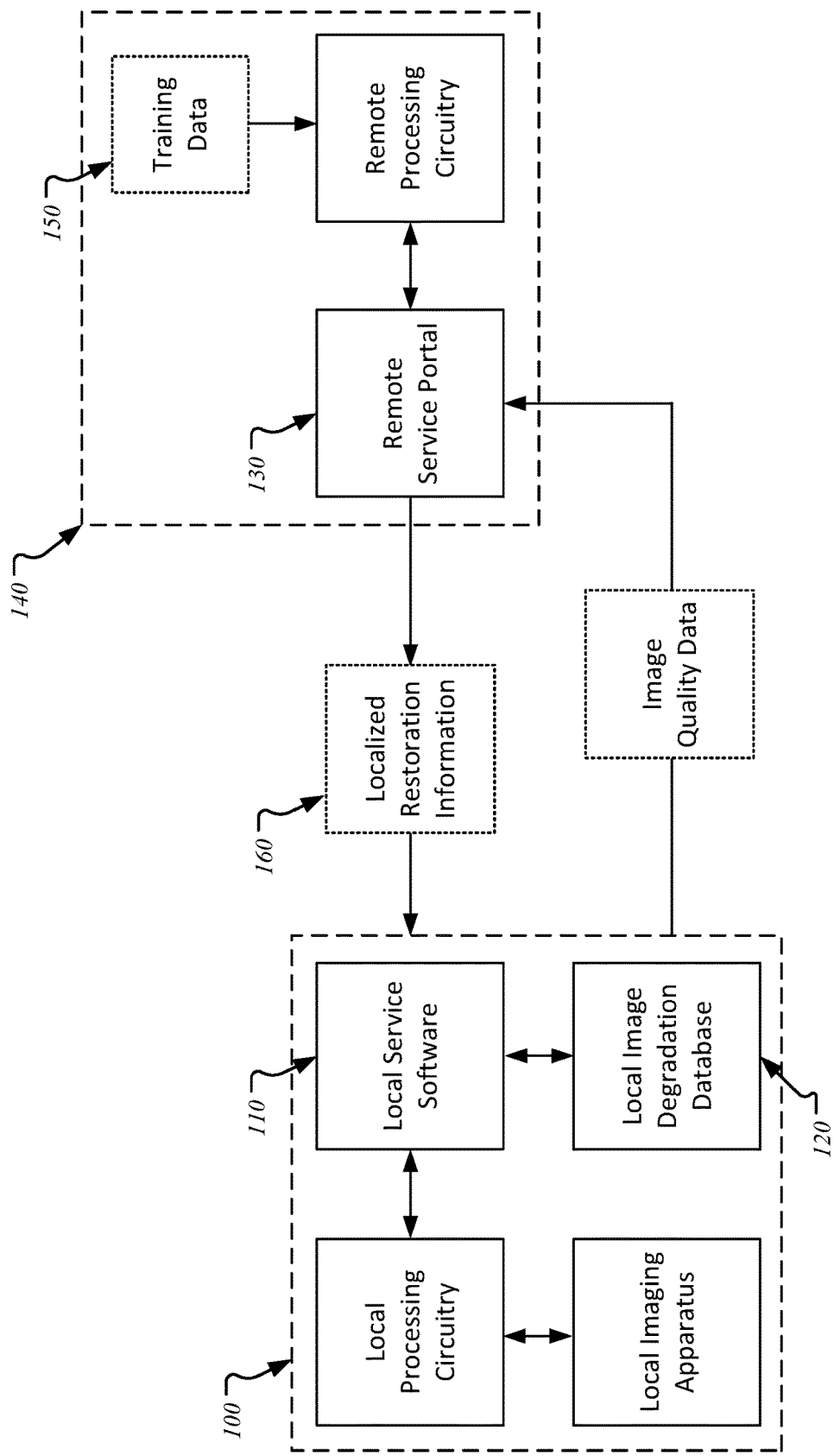
FIG. 2 shows a schematic of the system for automatic deployment of image restoration parameters, according to an embodiment of the present disclosure.

FIG. 2 shows a schematic of the system for automatic deployment of image restoration parameters, according to an embodiment of the present disclosure. In an embodiment, the local imaging system 100 can be a radiology system for imaging patients or objects and include an imaging apparatus and local processing circuitry. For example, the imaging apparatus can be configured for magnetic resonance imaging (MM), positron emission tomography (PET), X-ray fluoroscopy, computed tomography (CT), or a combination thereof. For example, the combination can be a PET and CT imaging apparatus. The imaging apparatus can be configured to emit predetermined electromagnetic radiation via a radiation source and detect the electromagnetic radiation via a plurality of detector elements to generate, via the local processing circuitry, an image of an object disposed between the radiation source and the plurality of detector elements. The local processing circuitry can be further configured to obtain, among others, image quality data related to the generated image based on the obtained projection data, signal gain parameters, image resolution parameters, signal noise parameters, and imaging parameters. As used herein, obtaining the image quality data can include reading from volatile memory, reading from non-volatile memory, reading from a user-input device, streaming data over a peer-to-peer or networked connection, etc. The signal noise parameters can include, for example, noise characteristics including noise power spectra (NPS), and noise correction coefficients, or any combination thereof. Additionally, the image resolution parameters can include a modulation transfer function (MTF). The image of the image quality dataset can be obtained by performing reconstruction of the projection data, or be the projection data itself. The local imaging system 100 can be configured to transmit the image quality data as well as receive data from another device. For example, local service software 110 (see FIG. 2) can act as the interface between the local imaging system 100 and the remote server 140. Alternatively, the local processing circuitry can communicate directly with the remote server 140. The local service software 110 can be implemented on the local processing circuitry. For example, the local service software 110 can transmit the image quality data to the remote server 140 and similarly receive data from the remote server 140.

It may be appreciated that the projection data need not be obtained using a particular image restoration model (e.g. a noise model), as it can be reflective of the image restoration model. The image restoration (or noise) model can allow an updated image restoration model to be produced in the form of a neural network and replace an existing image restoration model (see below). Thus, in some embodiments, the image restoration model need not be sent with the image quality data.

In an embodiment, the remote server 140 can include remote processing circuitry and a remote service portal 130. A neural network can be implemented on the remote processing circuitry and the remote processing circuitry can include instructions to perform application of the neural network. The remote processing circuitry can be configured to apply the neural network to data received, such as the image quality data or a set of training data 150. For example, the training data 150 can include de-noised images to which noise is introduced via known noise characteristics. The remote service portal 130 can be configured to interface with the local imaging system 100 to transmit and receive data. The training data 150 can be local to the remote server 140, connected by any appropriate link, including SATA, SAS, LAN, WLAN, or served from a different location.

The method and system described herein enables individualized training of the neural network based on image degradation characteristics (such as noise or the imager point spread function) collected at the time the local imaging system 100 is calibrated and turned over to an operator for general use.

At a predetermined time for calibration of the local imaging system 100, for example, during installation or routine service, the image quality data including the scan parameters and the image restoration model can be collected. The image restoration model can include one or more NPS or other noise measurements (such as quantum and electronic noise levels), each corresponding to unique scan parameters/acquisition modes (e.g. scan length, scan size, dose, etc.) for the respective local imaging system 100. In addition, the image quality data can include other imaging models, such as a point spread function. In one example, a biplane angiographic X-ray system can collect the image restoration model for each of its detectors for both high and low X-ray doses, but not at every possible dose in between. A local image degradation database 120 can associate each detector's image restoration model with the acquisition mode used and store a history of this correlation. For example, the history can be stored in volatile memory, non-volatile memory, etc. Additional data not related directly to noise, such as the point spread function and usage statistics, can also be associated with the individual acquisition modes used. When calibration of the local imaging system 100 has been completed to the satisfaction of the service technician, the local imaging system 100 can notify the remote server 140 that a new calibration has been performed.

The remote server 140 can respond to notification of the new calibration by requesting saved data (i.e. the image quality data) from the local imaging system 100 over a network connecting the local imaging system 100 and the remote server 140. For example, a computer network communicatively coupled as previously described may be used. In another example, the image quality data can be saved on a storage medium and physically transferred to the remote server 140. For example, the technician can transport the storage medium to the remote server 140 or mail the storage medium to the remove server 140. The storage medium can be, for example, a compact disc (CD), a Blu-ray disc, or a universal serial bus (USB) drive. The saved data can be used to generate the training data 150 and schedule either a new training of an image restoration neural network or fine tuning of a partially trained neural network. The result of the training can be localized restoration information 160, which can be transmitted to the local imaging system 100. The localized restoration information 160 can include, for example, a new local restoration model being a calculated neural network, improved noise coefficients for a noise correction process performed by the local imaging system 100, improved scan parameters for the local imaging apparatus, or any combination thereof, as well as the weighting coefficients and connections of the remotely calculated new local restoration model for locally generating improved noise coefficients for a noise correction process performed by the local imaging system 100, improved scan parameters for the local imaging apparatus, or any combination thereof. In one example, the local imaging system 100 hosts a fixed architecture neural network and only the updated noise coefficients for the fixed architecture neural network can be sent in the localized restoration information 160. In one example, the updated noise coefficients are sent to the local imaging system 100 along with the artificial neural network.

A history of the localized restoration information 160 versions can be optionally saved at the local imaging system 100, for example in the local image degradation database 120, for the purpose of creating restore points. While this process can be fully automated, some embodiments can call for operator intervention to perform training and update the local imaging system 100. Should it be necessary to revert any one of the local imaging systems 100-100n to a restore point, the restore points will allow the reversion to the previous state.

Furthermore, the local imaging system 100 can, at a predetermined time (e.g. system boot, subsystem boot, on demand, scheduled, etc.) load the updated localized restoration information 160, correlating the localized restoration information 160 with the respective acquisition modes and image restoration processing used. After the local imaging system 100 has been updated, the local imaging system 100 can additionally perform image quality checks on the new localized restoration information 160 to ensure that the obtained images are not degraded by the updated localized restoration information 160. These quality checks may be fully automated, or may require manual user intervention and approval.

In the case of an automated image quality check, a newly obtained image can be processed with both the previous and new localized restoration information 160 (including previous and new image restoration models as well as previous and new imaging parameters, i.e. the neural network), and the system can calculate image quality measurements including at least one of signal-to-noise ratio (SNR) and contrast-to-noise ratio (CNR). In one embodiment, the local imaging system 100 can locate a flat ("background") region of the image and compute a standard deviation of pixels in both restored images as proxies for the SNR. The local imaging system 100 may additionally locate an object of high contrast within the image (e.g., a guide wire) and assess a contrast based on strength of visibility of the object within the restored images. These measurements can be the basis for accepting or rejecting the newly implemented localized restoration information 160, either automatically or with approval of the operator.

In the case of partially automated image quality checks, a technician (such as a service technician) can obtain a nearly defect- or noise-free image by acquiring several frames of a stationary object (e.g. a phantom), the average of which can be treated as a ground truth from which SNR and CNR of the restored images can be calculated. The data of the stationary object can be the basis for accepting or rejecting the newly implemented localized restoration information 160, either automatically or with approval of the operator.

In the case of a fully manual image quality check, the technician can acquire an image which can be processed by both the local imaging system 100 and the remote system 140, and presented to the technician such that the localized restoration information 160 to use can be selected by choosing the better image, which selects the corresponding neural network, imaging parameters, and image restoration models.

Upon approval of the improved image quality using the updated localized restoration information 160, the previous version of the localized restoration information can be replaced by the updated localized restoration information 160 and the previous version of the localized restoration information can be stored in the local image degradation database 120. For example, the imaging parameters can be updated, such as updated scan length and updated scan dose. For example, the image restoration models can be updated, such as updated noise characteristics, updated noise coefficients, and updated NPS.

In an embodiment, the entire process of obtaining the image quality data from the local imaging system 100, transmitting the image quality data to the remote server 140, and receiving the updated localized restoration information 160 to update the local imaging system 100 can be fully automated. That is, upon determining no humans are within a predetermined area of the local imaging system 100, a self-calibration can be initiated automatically by the local imaging system 100 using a phantom for the object. In such a scenario, the local imaging system 100 can further include a robotic arm. The robotic arm can be configured to dispose the phantom in an imaging area of the local imaging system 100. Subsequently, an image of the phantom can be obtained and the image quality data can be transmitted to the remote server 140. This can be advantageous for performing more frequent calibrations of the system without the need for manual user input. For example, the automatic calibration can be performed when an imaging center is closed. The updated localized restoration information 160 can be automatically applied, or user input can be requested to ensure the localized restoration information 160 improves imaging results. During the fully automatic updating process, the process can immediately stop upon determining a human has entered the predetermined area of the local imaging system 100 to prevent exposing the human to harmful radiation.

Figure 3A:
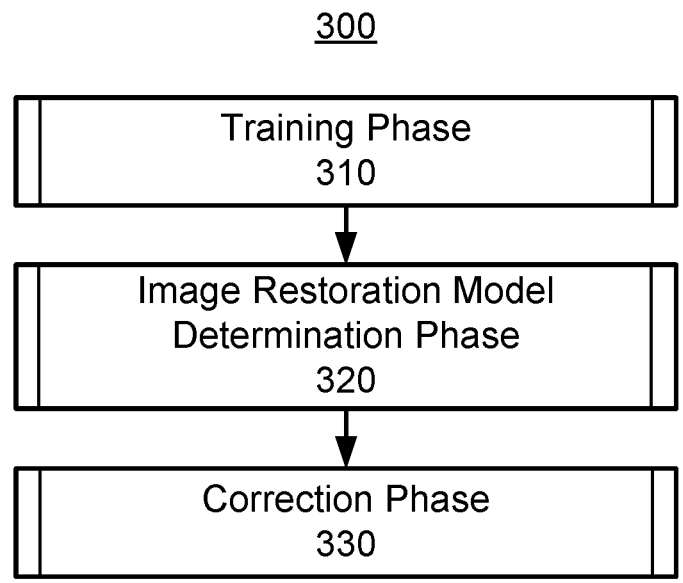
FIG. 3A provides a high-level framework for training a neural network for image restoration given an image quality dataset, according to an embodiment of the present disclosure.

FIG. 3A provides a high-level framework for training a neural network for image restoration modeling. The neural network can be trained using a training dataset generated from ground truth image restoration models. In a training phase, at process 310, the training data 150 can be generated using ground truth image restoration models, and the ground truth image restoration models can be generated from, for example, a model-based noise estimation method. This training data 150 can then be used to train the neural network. In an image restoration model determination phase, at process 320, image quality data from imaging an object or patient can be processed and then applied to the trained neural network with the result from the neural network being the updated local restoration model. Subsequently, in a correction phase at step 330 of process 300, correction of the local imaging system 100 can be performed to reduce or remove the image quality degradation factors, such as noise, from subsequent imaging, and an improved image can then be obtained.

Figure 3B:
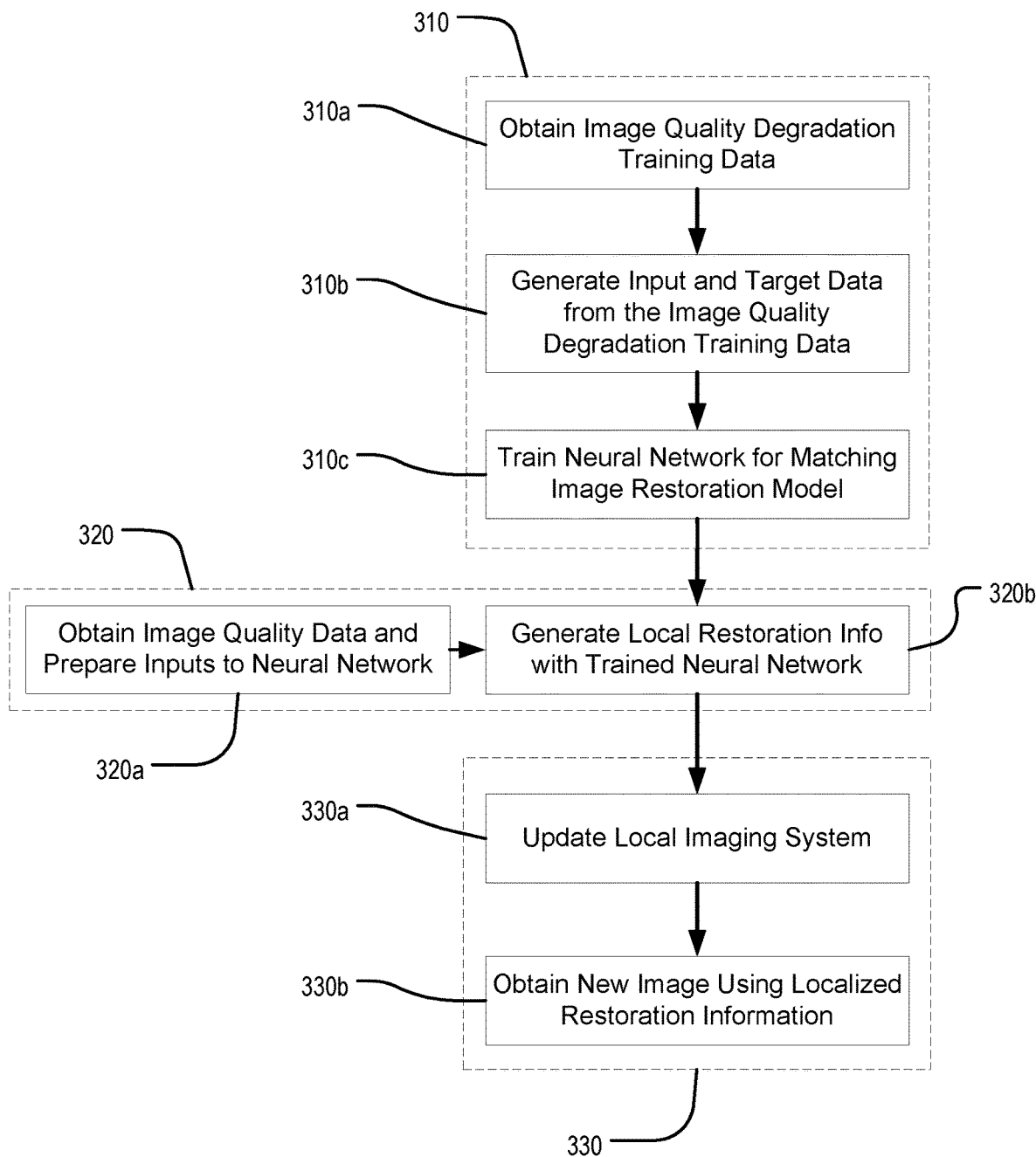
FIG. 3B provides a low-level flow diagram for the image quality estimation and correction method, according to an embodiment of the present disclosure.

FIG. 3B provides a low-level flow diagram for the image quality degradation estimation and restoration/correction method.

In step 310a of process 310, training data can be obtained. A large image quality degradation training database (e.g. the local image degradation database 120), which includes, for example, a plurality of sets of training data 150, can be used to account for the several factors upon which image degradation can depend, including: quantum noise, electronic detector noise, x-ray beam filtration, and patient geometry. To this end and according to an embodiment, a training database can include a plurality of images of phantoms and a plurality of images of patients, each with and without image restoration/correction. Each image of the plurality of phantom images can be selected according to a pre-determined human anatomy through modulation of the shape, size, and material each phantom is constructed from. In addition, and in consideration of a representative population of patients, the plurality of images of patients can be selected to include patients of simple and complex anatomy, the training data including typical patient data with variations including, among others, organ distribution, size, metal inclusion, and contrast.

In step 310b of process 310, the training data 150 for training the neural network is generated from the training data 150. To train the neural network, the training data 150 includes input data paired with target data, such that when the neural network is trained applying the input data to the neural network generates a result that matches the target data as closely as possible. To this end, the input data to the neural network can be restored images, such as de-noised images, of patients or phantoms with degradation introduced according to known parameters. Further, the target data of the neural network are estimates of the degradation characteristics.

In step 310c of process 310, the training data 150, including the target images paired with respective sets of input images, can be used for training and optimization of the neural network. Generally, training of the neural network can proceed according to techniques understood by one of ordinary skill in the art, and the training of the neural network is not limited to the specific examples provided herein, which are provide as non-limiting examples to illustrate some ways in which the training can be performed.

Following training of the neural network in the training phase of process 310, an image restoration model determination phase of process 320 can be performed.

In step 320a of process 320, image quality degradation data from the image quality data can be obtained and prepared for application to the trained neural network. For example, the image quality degradation data can include noise data, and the noise data can be separated into NPS, noise coefficients, etc. The prepared image quality degradation data can be segmented into components having a same structure as the input images/data in the training data 150. The process of preparing the image quality degradation data can include any one or more of the methods described above for preparing the input images/data of the training data 150, or any other methods.

In step 320b of process 320, the prepared image quality degradation data can be applied to the trained neural network and localized restoration information 160 can be generated. The output from the trained neural network can be used to correct the image quality data (including noisy images) obtained at step 310a by removing the noise. For example, by eliminating the noise from the uncorrected noisy images, the noise characteristics can be isolated.

In step 330a of process 330, the generated localized restoration information 160 output from the trained neural network and the resulting updated image restoration model can be used to correct the local imaging system 100 and subsequent image capturing events.

In step 330b of process 330, the isolated image quality degradation characteristics can be used to obtain a new image using the localized restoration information 160 at the local imaging system 100 that includes reduced or removed image quality degradation for subsequent image capture events.

Figure 4:
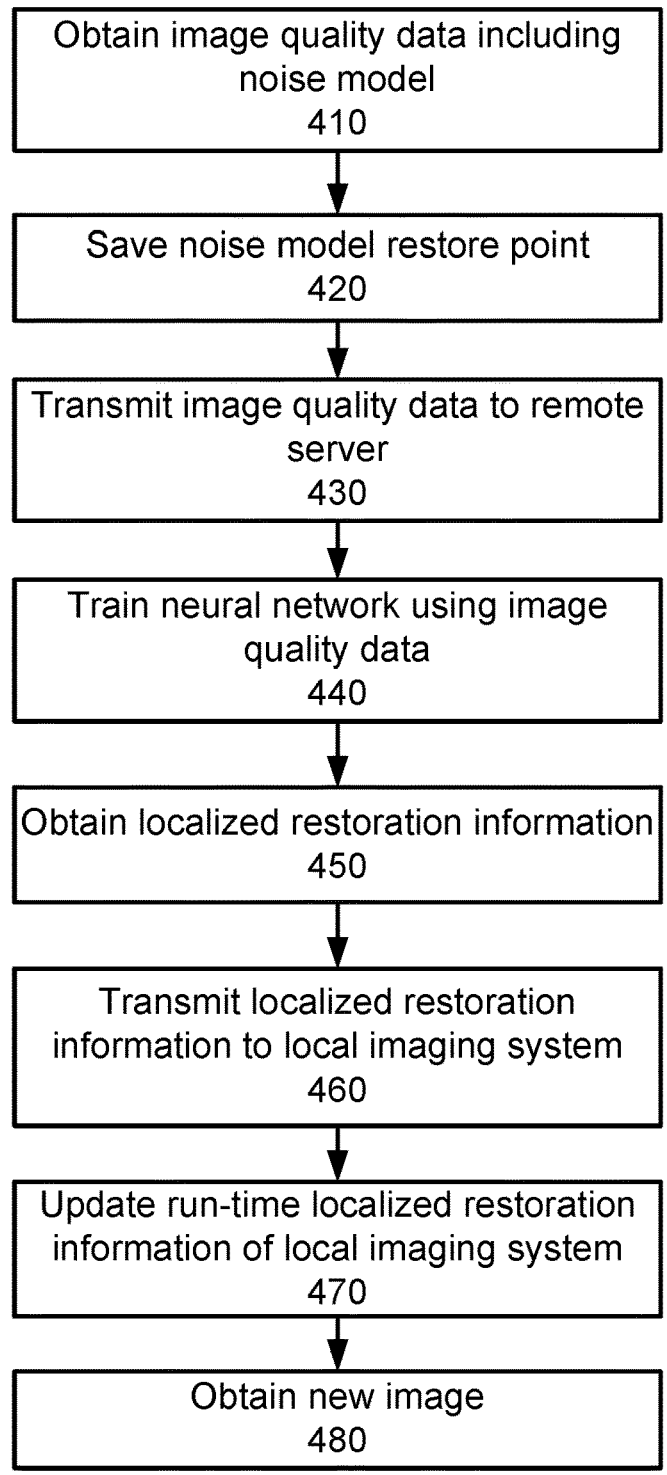
FIG. 4 shows a non-limiting example of a flow chart for a method of determining noise characteristics and automatically deploying image restoration parameters, according to an embodiment of the present disclosure.

FIG. 4 shows a non-limiting example of a flow chart for a method 400 of determining image quality degradation and automatically deploying image restoration parameters, according to an embodiment of the present disclosure. In an embodiment, the method 400 can be performed at a predetermined time interval, such as a scheduled maintenance, or on-demand when desired by the technician or operator. In step 410, the image quality data from the local imaging system 100 can be obtained. For example, the image quality data can include an existing image restoration model or other imaging models. The image restoration model can include an NPS or other noise measurements corresponding to a unique image acquisition configuration. In step 420, a restore point of the local imaging system 100 can be saved in the event of a future desire to revert the local imaging system 100 back to a previous configuration. The restore point can capture a "snapshot" of the settings of the local imaging system 100, including the restoration model currently utilized for image generation. In step 430, the image quality data can be transmitted to the remote server 140. In step 440, the neural network can be trained using the training data 150 and the image quality data. In step 450, the localized restoration information 160 can be obtained. In step 460, the localized restoration information 160 can be transmitted to the local imaging system 100. In step 470, the local imaging system 100 utilizing the previous imaging parameters can be updated using the local restoration model. In step 480, a new image can be obtained using the local imaging system 100 utilizing the updated localized restoration information 160 and imaging parameters.

Figure 5A:
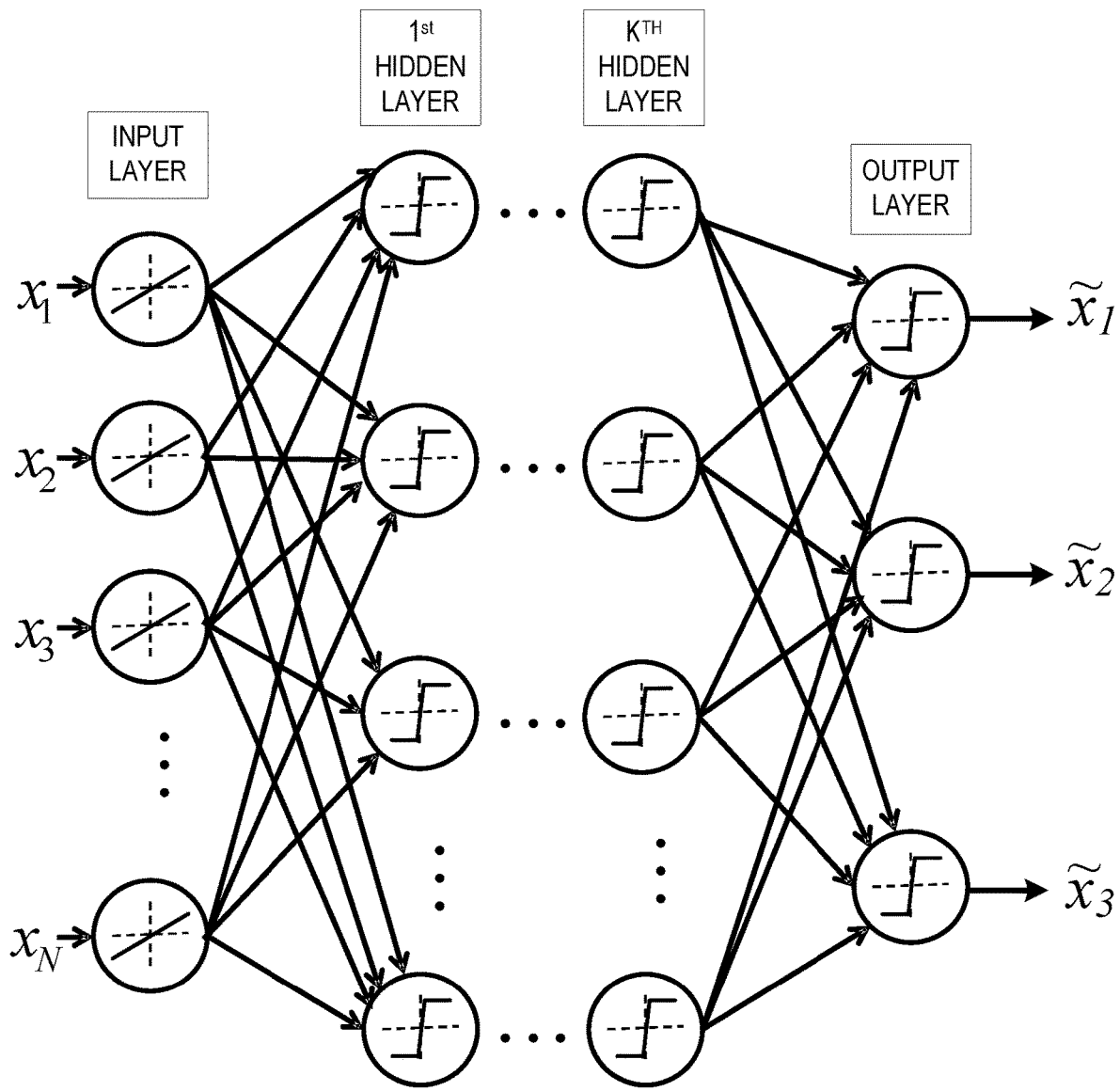
FIG. 5A shows an example of a general artificial neural network (ANN), according to an embodiment of the present disclosure.

FIG. 5A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers and is called an autoencoder. The neural network can have more than three layers of neurons and have as many output neurons $\hat{x}_N$ as input neurons, wherein N is the number of pixels in the training image. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can be further defined as a composition of other functions. This can be conveniently represented as a network structure, with arrows depicting the dependencies between variables, as shown in FIG. 5A. For example, the ANN can use a nonlinear weighted sum, wherein $m(x)=K(\Sigma_i w_i n_i(x))$ and where K (commonly referred to as the activation function) is some predefined function, such as the hyperbolic tangent.

In FIG. 5A, the neurons (i.e., nodes) are depicted by circles around a threshold function. For the non-limiting example shown in FIG. 5A, the inputs are depicted as circles around a linear function and the arrows indicate directed communications between neurons. In certain implementations, the neural network is a feedforward network as exemplified in FIG. 2 (e.g., it can be represented as a directed acyclic graph).

The neural network of the present disclosure operates to achieve a specific task, such as estimating noise characteristics in an image, by searching within the class of functions F to learn, using a set of observations, to find m*∈F, which solves the specific task in some optimal sense. For example, in certain implementations, this can be achieved by defining a cost function C:F→m such that, for the optimal solution m*, $C(m^*) \leq C(m) \forall m \in F$ (i.e., no solution has a cost less than the cost of the optimal solution). The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training data 150).

FIG. 5B is a block diagram of an exemplary X-ray apparatus that can be used to perform the methods described herein, e.g., method 400, according to an embodiment of the present disclosure. The X-ray apparatus includes a gantry 500 and a console 520. The gantry 500 includes an X-ray source system 511, a beam-shaping system 512, a patient table 513, a detection system 514, and a gantry control transmission circuitry 515.

The X-ray source system 511 includes a high voltage generator 510 and an X-ray tube 501. The high voltage generator 510 applies a high voltage to the X-ray tube 501 under the control of the gantry control transmission circuitry 515, and supplies a filament current to the X-ray tube 501 under the control of the gantry control transmission circuitry 515. The X-ray tube 501 generates X-rays to irradiate an object OBJ upon receiving a trigger from the high voltage generator 510.

The collimation system 512 includes a beam filter/attenuator 516 which modifies the spectrum of the X-ray beam from the X-ray tube 501. A collimator 517 opens and closes in accordance with a field of view selected at the time of the operation. The collimation system 512 forms an X-ray beam and irradiates the object OBJ with X-rays.

The detection system 514 includes a two-dimensional array of detection elements (pixels) configured to absorb the X-ray transmitted through the object OBJ and generate an electrical charge signal proportional to the absorbed X-ray intensity. The electrical signal of each pixel is amplified and converted to a digital number by A/D converters.

For example, the detection system 514 includes the detector 503 and a data acquisition system (DAS) 504. The detector 503 detects the X-rays generated from the X-ray tube 501. The detector 503 is equipped with a plurality of detection elements arrayed two-dimensionally. Each detection element detects the X-rays generated from the X-ray tube 501 and generates an electrical signal (current signal) corresponding to the intensity of the detected X-rays.

The generated electrical signal is supplied to the DAS 504. The DAS 504 includes an amplifier 504A, an A/D converter 504B, and a control panel 504C. The DAS 504 reads out electrical signals via the detector 503 and obtains the readout electrical signals, via the control panel 504C. The gantry control transmission circuitry 515 controls the high voltage generator 510, the attenuator 516, the collimator 517, and the control panel 504 to execute X-ray imaging.

The console 520 includes pre-processing circuitry 521, image-processing circuitry 522, a display 523, an operation device 524, data storage 525, and system control circuitry 526.

The pre-processing circuitry 521 executes pre-processing, such as sensitivity correction for raw data supplied from the detection system 514, via the gantry control transmission circuitry 515.

The image-processing circuitry 522 can perform the image-processing methods described herein, including methods 200, 300, and 400.

The display 523 displays the image generated by the image-processing circuitry 522.

The operation circuitry 524 accepts various types of commands and information inputs from a user, via an input device.

The data storage (memory) 525 stores the raw data and various types of data, such as projection data and images. In addition, the data storage 525 stores control programs for the X-ray apparatus, and control programs for performing the image-processing methods described herein.

The system control circuitry 526 functions as the main circuitry of the X-ray apparatus. The system control circuitry 526 reads out control programs stored in the data storage 525 and loads the programs into the memory. The system control circuitry 526 controls the respective circuitry in the X-ray apparatus in accordance with the loaded control programs.

In the preceding description, specific details have been set forth, such as a particular geometry of a processing system and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Embodiments of the present disclosure may also be as set forth in the following parentheticals.

(1) A method, comprising: obtaining, at a local imaging system, projection data for an object representing an intensity of radiation detected along a plurality of rays through the object using a first set of imaging parameters; transmitting an image quality dataset related to the obtained projection data to a remote server; generating, via the remote server, localized restoration information based on the received image quality dataset; transferring the localized restoration information from the remote server to the local imaging system; and updating the local imaging system using the localized restoration information.

(2) The method of (1), wherein the object is a phantom, and the step of obtaining projection data further comprises upon determining a human is not disposed in a predetermined area of the local imaging system, obtaining the projection data of the phantom without human initialization.

(3) The method of (2), wherein the step of obtaining projection data further comprises disposing the phantom in an imaging area robotically.

(4) The method of any one of (1) to (3), further comprising transmitting the first set of imaging parameters from the local imaging system to the remote server; and saving the first set of imaging parameters as a first restore point.

(5) The method of any one of (1) to (4), wherein the localized restoration information includes a second set of imaging parameters and updating the local imaging system further comprises replacing the first set of imaging parameters with the second set of imaging parameters.

(6) The method of any one of (1) to (5), the projection data is obtained using a first image restoration model, the localized restoration information includes a second image restoration model, and updating the local imaging system comprises replacing the first image restoration model with the second image restoration model.

(7) The method of any one of (1) to (6), wherein the image quality dataset includes an image obtained by performing reconstruction of the projection data.

(8) The method of any one of (1) to (7), further comprising obtaining, at the local imaging system, an image using the localized restoration information received from the remote server.

(9) The method of any one of (1) to (8), wherein the step of transferring the localized restoration information to the local imaging system is performed using a computer network.

(10) The method of any one of (1) to (9), wherein the step of generating the localized restoration information further comprises calculating, via the remote server, an artificial neural network based on the received image quality dataset to generate the localized restoration information.

(11) An imaging system, comprising: processing circuitry configured to obtain, at the local imaging system, projection data for an object representing an intensity of radiation detected along a plurality of rays through the object using a first set of imaging parameters; transmit an image quality dataset related to the obtained projection data to a remote server; generate, via the remote server, localized restoration information based on the received image quality dataset; transfer the localized restoration information from the remote server to the local imaging system; and update the local imaging system using the localized restoration information.

(12) The system of (11), wherein the object is a phantom, and the processing circuitry is further configured to obtain the projection data by, upon determining a human is not disposed in a predetermined area of the local imaging system, obtain the projection data of the phantom without human initialization.

(13) The system of (12), wherein the processing circuitry is further configured to obtain projection data by disposing the phantom in an imaging area robotically.

(14) The system of any one of (11) to (13), wherein the processing circuitry is further configured to transmit the first set of imaging parameters from the local imaging system to the remote server, and save the first set of imaging parameters as a first restore point.

(15) The system of any one of (11) to (14), wherein the localized restoration information includes a second set of imaging parameters and the processing circuitry is further configured to update the local imaging system by replacing the first set of imaging parameters with the second set of imaging parameters.

(16) The system of any one of (11) to (15), wherein the projection data is obtained using a first image restoration model, the localized restoration information includes a second image restoration model, and the processing circuitry is further configured to update the local imaging system by replacing the first image restoration model with the second image restoration model.

(17) The system of any one of (11) to (16), wherein the image quality dataset includes an image obtained by performing reconstruction of the projection data.

(18) The system of any one of (11) to (17), wherein the processing circuitry is further configured to obtain, at the local imaging system, an image using the localized restoration information.

(19) A non-transitory computer-readable storage medium including executable instructions, which when executed by circuitry, cause the circuitry to perform a method of reducing in an imaging system, comprising: obtaining, at a local imaging system, projection data for an object representing an intensity of radiation detected along a plurality of rays through the object using a first set of imaging parameters; transmitting an image quality dataset related to the obtained projection data to a remote server; generating, via the remote server, localized restoration information based on the received image quality dataset; transferring the localized restoration information from the remote server to the local imaging system; and updating the local imaging system using the localized restoration information.

(20) The non-transitory computer-readable storage medium of (19), wherein the object is a phantom, and the step of obtaining projection data further comprises upon determining a human is not disposed in a predetermined area of the local imaging system, obtaining the projection data of the phantom without human initialization.

(21) The method of any one of (1) to (10), wherein the step of transferring the localized restoration information to the local imaging system is performed using a storage medium.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

What is claimed is:

1. A method, comprising:
   obtaining, at a local imaging system, projection data for an object representing an intensity of radiation detected along a plurality of rays through the object using a first set of imaging parameters;
   transmitting an image quality dataset related to the obtained projection data to a remote server, the image quality dataset including at least one parameter, of the first set of imaging parameters, involved in obtaining the projection data;
   generating, via the remote server, localized restoration information for calibrating the local imaging system based on the received image quality dataset, the localized restoration information being configured to maintain a constant image quality of the projection data obtained by the local imaging system;
   transferring the localized restoration information from the remote server to the local imaging system; and
   updating at least one setting related to the obtaining of the projection data on the local imaging system using the localized restoration information.

2. The method of claim 1, wherein
   the object is a phantom, and
   the step of obtaining the projection data further comprises upon determining a human is not disposed in a predetermined area of the local imaging system, obtaining the projection data of the phantom without human initialization.

3. The method of claim 2, wherein the step of obtaining the projection data further comprises disposing the phantom in an imaging area robotically.

4. The method of claim 1, further comprising:
   transmitting the first set of imaging parameters from the local imaging system to the remote server; and
   saving the first set of imaging parameters as a first restore point.

5. The method of claim 1, wherein the localized restoration information includes a second set of imaging parameters, and the step of updating the at least one setting related to the obtaining of the projection data on the local imaging system further comprises replacing the first set of imaging parameters with the second set of imaging parameters.

6. The method of claim 1, wherein
   the projection data is obtained using a first image restoration model,
   the localized restoration information includes a second image restoration model, and
   the step of updating the at least one setting related to the obtaining of the projection data on the local imaging system further comprises replacing the first image restoration model with the second image restoration model.

7. The method of claim 1, wherein the image quality dataset includes an image obtained by performing reconstruction of the projection data.

8. The method of claim 1, further comprising:
   obtaining, at the local imaging system, an image using the localized restoration information received from the remote server.

9. The method of claim 1, wherein
   the at least one parameter in the image quality dataset is a signal noise parameter,
   the localized restoration information is generated for calibrating the local imaging system based on the received image quality dataset, and
   the localized restoration information is configured to maintain a constant image quality of the projection data obtained by the local imaging system.

10. The method of claim 1, wherein the step of generating the localized restoration information further comprises calculating, via the remote server, an artificial neural network based on the received image quality dataset to generate the localized restoration information.

11. The method of claim 1, comprising:
    accepting or rejecting the restoration information based upon image quality measurements made using an image with the restoration information and an image processed with previously received restoration information.

12. The method of claim 11, comprising:
    performing the image quality measurements using a stationary object.

13. The method of claim 1, further comprising:
    storing, in a memory, first localized restoration information used to update the at least one setting;
    determining whether projection data obtained at the local imaging system that was updated using second localized restoration information generated later than the first localized restoration information has been degraded; and
    upon determining the projection data obtained at the local imaging system that was updated using the second localized restoration information has been degraded, updating the at least one setting related to the obtaining of the projection data on the local imaging system using the first localized restoration information.

14. An imaging system, comprising:
processing circuitry configured to
obtain, at a local imaging system, projection data for an object representing an intensity of radiation detected along a plurality of rays through the object using a first set of imaging parameters;
transmit an image quality dataset related to the obtained projection data to a remote server, the image quality dataset including at least one parameter, of the first set of imaging parameters, involved in obtaining the projection data;
generate, via the remote server, localized restoration information for calibrating the local imaging system based on the received image quality dataset, the localized restoration information being configured to maintain a constant image quality of the projection data obtained by the local imaging system;
transfer the localized restoration information from the remote server to the local imaging system; and
update at least one setting related to the obtaining of the projection data on the local imaging system using the localized restoration information.

15. The system of claim 14, wherein
the object is a phantom, and
the processing circuitry is further configured to obtain the projection data by, upon determining a human is not disposed in a predetermined area of the local imaging system, obtain the projection data of the phantom without human initialization.

16. The system of claim 15, wherein the processing circuitry is further configured to obtain the projection data by disposing the phantom in an imaging area robotically.

17. The system of claim 14, wherein the processing circuitry is further configured to
transmit the first set of imaging parameters from the local imaging system to the remote server, and
save the first set of imaging parameters as a first restore point.

18. The system of claim 14, wherein the localized restoration information includes a second set of imaging parameters, and the processing circuitry is further configured to update the at least one setting related to the obtaining of the projection data on the local imaging system by replacing the first set of imaging parameters with the second set of imaging parameters.

19. The system of claim 14, wherein
the projection data is obtained using a first image restoration model,
the localized restoration information includes a second image restoration model, and
the processing circuitry is further configured to update the at least one setting related to the obtaining of the projection data on the local imaging system by replacing the first image restoration model with the second image restoration model.

20. The system of claim 14, wherein the image quality dataset transmitted by the processing circuitry includes an image obtained by performing reconstruction of the projection data.

21. The system of claim 14, wherein the processing circuitry is further configured to obtain, at the local imaging system, an image using the localized restoration information.

22. The system of claim 14, further comprising:
a memory to store first localized restoration information used to update the at least one setting, wherein
the processing circuitry is further configured to
determine whether projection data obtained at the local imaging system that was updated using second localized restoration information generated later than the first localized restoration information has been degraded; and
upon determining the projection data obtained at the local imaging system that was updated using the second localized restoration information has been degraded, update the at least one setting related to the obtaining of the projection data on the local imaging system using the first localized restoration information.

23. A non-transitory computer-readable storage medium including executable instructions, which when executed by circuitry, cause the circuitry to perform a method of reducing in an imaging system, the method comprising:
obtaining, at a local imaging system, projection data for an object representing an intensity of radiation detected along a plurality of rays through the object using a first set of imaging parameters;
transmitting an image quality dataset related to the obtained projection data to a remote server, the image quality dataset including at least one parameter, of the first set of imaging parameters, involved in obtaining the projection data;
calculating, via the remote server, an artificial neural network based on the received image quality dataset to generate localized restoration information for calibrating the local imaging system, the localized restoration information being configured to maintain a constant image quality of the projection data obtained by the local imaging system;
transferring the localized restoration information from the remote server to the local imaging system; and
updating at least one setting related to the obtaining of the projection data on the local imaging system using the localized restoration information.

24. The non-transitory computer-readable storage medium according to claim 23, wherein the object is a phantom, and
the step of obtaining the projection data further comprises upon determining a human is not disposed in a predetermined area of the local imaging system, obtaining the projection data of the phantom without human initialization.

25. The non-transitory computer-readable storage medium according to claim 23, wherein the method further comprises:
storing first localized restoration information used to update the at least one setting in a memory;
determining whether projection data obtained at the local imaging system that was updated using second localized restoration information generated later than the first localized restoration information has been degraded; and
upon determining the projection data obtained at the local imaging system that was updated using the second localized restoration information has been degraded, updating the at least one setting related to the obtaining of the projection data on the local imaging system using the first localized restoration information.

* * * * *